(12) United States Patent
Harris et al.

(10) Patent No.: US 6,531,489 B2
(45) Date of Patent: Mar. 11, 2003

(54) SINGLE ISOMER METHYLPHENIDATE AND RESOLUTION PROCESS

(75) Inventors: Michael Christopher James Harris, Cambridge (GB); Hooshang Zavareh, Cambridge (GB)

(73) Assignee: Chiroscience, Ltd. (GB)

( * ) Notice: Subject to any disclaimer, the term of this patent is extended or adjusted under 35 U.S.C. 154(b) by 0 days.

(21) Appl. No.: 09/836,731

(22) Filed: Apr. 17, 2001

(65) Prior Publication Data

US 2001/0014687 A1 Aug. 16, 2001

Related U.S. Application Data

(63) Continuation of application No. 08/788,881, filed on Jan. 22, 1997, now Pat. No. 6,242,464.
(60) Provisional application No. 60/013,779, filed on Mar. 21, 1996.

(51) Int. Cl.$^7$ ................. A61K 31/445; A61K 31/47; A61K 31/21; C07D 211/00; C07D 295/00
(52) U.S. Cl. ................. 514/317; 514/313; 514/513; 546/184
(58) Field of Search ................. 514/317, 313, 514/513; 546/184

(56) References Cited

U.S. PATENT DOCUMENTS

| | | | |
|---|---|---|---|
| 2,957,880 A | 10/1960 | Rometsch | 200/249 |
| 5,093,350 A | 3/1992 | Huang et al. | 511/44 |
| 5,733,756 A | 3/1998 | Zeitlin et al. | 435/122 |

FOREIGN PATENT DOCUMENTS

| | | |
|---|---|---|
| JP | 7247286 | 9/1995 |
| WO | 9531436 | 11/1995 |

OTHER PUBLICATIONS

Shafi'ee, Abbas et al. (1967) "Absolute Configurations of Enantiomeric Pheniramines, Methylphenidates, and Pipradrols" *J. Pharm. Sci.* 56(12):1689–1690.

Ding, Y–S. et al. (1994) "Synthesis of the Racemate and Individual Enantiomers of [$^{11}$C] Methylphenidate for Studying Presynaptic Dopamingergic Neuron with Positron Emission Tomography" *Journal of Labelled Compounds and Radiopharmaceuticals* 34(10):989–997.

Patrick, K. et al. (1987) "Pharmacology of the Enantiomers of threo–Methylphenidate" *The Journal of Pharmacology and Experimental Therapeutics* 241(1):152–158.

Deutsch, H. et al. (1996) "Synthesis and Pharmacology of Potential Cocaine Antagonists. 2. Structure–Activity Relationship Studies of Aromatic Ring–Substituted Methylphenidate Analogs" *J. Med. Chem* 39:1201–1209.

Aoyama, T. et al. (1989) "Gas Chromatographic–Mass Spectrometric Analysis of threo–Methylphenidate Enantiomers in Plasma" *Journal of Chromatography* 494:420–423.

*Primary Examiner*—Russell Travers
(74) *Attorney, Agent, or Firm*—Saliwanchik, Lloyd & Saliwanchik

(57) ABSTRACT

Single isomer methylphenidate, selected from the d- and l-threo-enantiomers, has been obtained in purified form, to the extent of less than 2% by weight of a contaminant selected from resolving agent and ritalinic acid. This is achieved by resolution of a mixture of enantiomers using an O, O'-diaroyltartaric acid as resolving agent.

11 Claims, No Drawings

SINGLE ISOMER METHYLPHENIDATE AND RESOLUTION PROCESS

CROSS-REFERENCE TO RELATED APPLICATIONS

This application is a continuation of U.S. application Ser. No. 08/788,881, filed Jan. 22, 1997, issued now U.S. Pat. No. 6,242,464, which claims the benefit of provisional U.S. application Serial No. 60/013,779, filed Mar. 21, 1996.

FIELD OF THE INVENTION

This invention relates to the resolution of threo methylphenidate via crystallisation of diastereomeric salts, and to the especially pure enantiomers thus obtained.

BACKGROUND OF THE INVENTION

Methylphenidate is a therapeutic agent that is widely used in the treatment of attention-deficient hyperactivity disorder. It is a controlled substance. Methylphenidate was first prepared as a mixture of the erythro and threo racemates. U.S. Pat. No. 2,957,880 discloses studies upon the two racemic mixtures, which revealed that the therapeutic activity resides in the threo diastereomer. It is now considered that it is the d-threo [or (R,R)] enantiomer that has the preferred therapeutic activity. Uses of this enantiomer are disclosed in PCT/GB96/01688, PCT/GB96/01689 and PCT/GB96/01690, the contents of which are incorporated herein by reference.

The resolution of threo methylphenidate can be achieved using the expensive resolving agent 1,1'-binaphthyl-2,2'-diyl hydrogen phosphate, a process first reported by Patrick et al (The Journal of Pharmacology and Experimental Therapeutics, 241:152–158 (1987)), and subsequently used by other workers in the field (e.g. Aoyama et al, Journal of Chromatography, 494:420 (1989)). This is perceived to be a more efficient procedure than the method disclosed in U.S. Pat. No. 2,957,880, wherein the corresponding amide of erythro methylphenidate (i.e. R-CONR$_2$ rather than R-CON$_2$Me) is resolved with tartaric acid prior to amide hydrolysis and equilibration at the benzylic centre, followed by esterification of the resultant threo-acid.

SUMMARY OF THE INVENTION

This invention is based upon the discovery that racemic threo methylphenidate can be resolved using inexpensive carboxylic acids, specifically O,O'-diaroyltartaric acids, with surprising efficiency. In one embodiment of the present invention, either D- or L-O,O-di-toluoyltartaric acid forms diastereomeric salts with threo-methylphenidate, and these salts are very readily separated.

An important consequence of this discovery is that the desired enantiomer is obtained in greater chemical purity than by any prior method. Thus, while the process of Patrick et al may give the desired product contaminated with resolving agent, this contaminant can only be removed by repeated extractions that cause hydrolysis of the ester, leaving ritalinic acid as a contaminant.

Needless to say, a product intended for administration to humans should be as pure as possible. Surprisingly, the process of this invention gives the desired enantiomer in very high chemical and enantiomeric purity. In particular, the product is substantially free of resolving agent and/or ritalinic acid (and/or the opposite enantiomer). This purity can be at least 98%, preferably at least 99%, more preferably at least 99.5%, and most preferably at least 99.9%. The product may be in free base form or as a pharmaceutically-acceptable salt, e.g. the hydrochloride.

DESCRIPTION OF THE INVENTION

The process of this invention may be carried out under conditions that are generally known to those skilled in the art of classical salt resolution procedures.

For example, a mixture of threo-methylphenidate and 1 molar equivalent of D-O,O-ditoluoyltartaric acid in an inert organic solvent is heated and then allowed to cool; the resultant precipitate is filtered, washed with an appropriate solvent and dried to afford directly a salt enriched in at least 97% ee d-threo-methylphenidate, i.e containing less than 1.5% of the opposite enantiomer. Enrichment to higher ee, e.g. at least 99%, can be simply achieved, by reslurrying in fresh solvent and filtering. This is a great improvement on the literature method using 1,1'-binaphthyl-2,2'-diyl hydrogen phosphate, described by Patrick et al, supra, in which the first crystallisation gave a salt corresponding to 85–90% ee material, and further recrystallisation of this material was necessary to raise the ee to 95–97%. The latter level of optical purity is achieved in the present invention in one crystallisation, with an overall higher yield. The method of this invention is therefore more efficient and more economical than the method described by Patrick et al.

Methylphenidate may initially be obtained as a salt of the resolving agent. This may be converted directly to the hydrochloride salt, or any other pharmaceutically-acceptable salt, by a salt exchange procedure. It may be preferable to release the free base, by salt cracking. If desired, the free base can then be converted to a salt form. All these procedures are known to those skilled in the art.

Further advantages of the present invention are as follows:

(i) Salt cracking at pH 9–10 is by addition of aqueous sodium hydroxide, whereas dilute aqueous sodium carbonate is needed for salts of the more base-labile 1,1'-binaphthyl-2,2'diyl hydrogen phosphate; this renders the novel process more volume efficient.

(ii) Lower volume of aqueous medium in (i) means fewer extractions into organic solvent (TBME rather than diethyl ether) to isolate methylphenidate free base.

(iii) Chemical robustness of DTTA allows for clean and efficient recovery.

Either isomer of methylphenidate can be easily obtained by this procedure, e.g. by simply using the D- or L-isomer of the diaroyl tartaric acid derivative as required.

Single isomer methylphenidate according to this invention, especially pure d-threo-methylphenidate, can be used in therapy for the same purposes as the racemate, e.g. in the treatment of ADHD or narcolepsy. The compound can be formulated with any suitable carrier, in any suitable dosage, as will be apparent to one of ordinary skill in the art. Reference in this context may be made to any of the three PCT Applications identified above.

The following Example illustrates the invention.

EXAMPLE

Ditoluoyl-D-tartaric acid (5.033 g, 12.4 mmol) was suspended in a solution of 2% methanol in acetone (10 ml), and a solution of threo-methylphenidate (2.9 g, 12.4 mmol) in the same solvent (10 ml) was added. The solution was gently warmed to reflux whereupon all the reagents dissolved. The solution was immediately cooled and crystals began to form. The solution was allowed to stand at 4° C. for 17 hours and was then filtered. The crystals were washed with acetone (3×15 ml) and dried in vacuo to yield the ditoluoyl-D-tartrate salt of d-threo methylphenidate (3.516 g, 44.3% by weight; corresponding to 97% ee d-threo methylphenidate, as determined by chiral HPLC after salt cracking). The mother liquors were dried in vacuo to yield the ditoluoyl-D-tartrate salt of l-threo-methylphenidate as a solid, dry form (4.508 g, 50.5% yield, 88% ee).

The ditoluoyl-D-tartrate salt of d-threo-methylphenidate (3.486 g), obtained as described above, was suspended in 2% methanol in acetone, and warmed to c. 40° C. and cooled. This did not dissolve the solid which was stirred at room temperature for 24 hours. The suspension was filtered, the solid washed with acetone (10 ml) and dried in vacua, to yield diastereomerically pure material (3.209 g, 92% recovery, corresponding to >99% ee d-threo-methylphenidate).

Repeating this protocol using isopropanol: methanol as the solvent, gave the same salt, on initial crystallisation, enriched in at least 98%. Reslurrying increased this.

For the purposes of comparison, USP grade dl-threo-methylphenidate hydrochloride (3.36 g) was dissolved in an aqueous solution of sodium carbonate (45 ml, 2% w/v), and the clear solution was extracted with diethyl ether (3×50 ml). The combined ethereal layers were dried ($MgSO_4$), filtered, and evaporated to dryness. The resulting pale yellow oil together with (R)-(−)-1,1'-binaphthyl-2,2'diyl hydrogen phosphate (3.36 g) were dissolved in a hot mixture of acetone/methanol (95:5). The solution was gently stirred and cooled to 5° C. and maintained for 12 hours. The resulting white crystals (2.98 g) were isolated by filtration and recrystallised from acetone/methanol (98:2). This product was then treated with a 2% aqueous solution of sodium carbonate and extracted with diethyl ether (4×50 ml). The combined ethereal layers were dried ($MgSO_4$) and filtered. An excess saturated solution of hydrogen chloride in ether was then added and the resulting hydrochloride salt was filtered, rinsed with ether, and recrystallised from methanol/ether. The resulting white crystalline product was analyzed by HPLC and proton NMR:

% w/w l-threo: 3.7% e.e.: 92.6% ritalinic acid: trace amount but not quantified by HPLC or NMR resolving agent: approximately 4% by NMR It should be understood that the examples and embodiments described herein are for illustrative purposes only and that various publications or changes in light thereof will be suggested to persons skilled in the art to be included within the spirit and purview of this application and the scope of the appended claims.

We claim:

1. A single isomer methylphenidate compound, selected from the group consisting of the d-threo- and l-threo-enantiomers, and pharmaceutically-acceptable salts thereof, wherein said compound is in combination with less than about 2% by weight of a contaminant selected from the group consisting of resolving agents and ritalinic acid.

2. The methylphenidate compound, according to claim 1, in combination with less than about 1% by weight of said contaminant.

3. The methylphenidate compound, according to claim 1, in combination with less than about 0.5% by weight of said contaminant.

4. The methylphenidate compound, according to claim 1, in combination with less than about 0.1% by weight of said contaminant.

5. The methylphenidate compound, according to claim 1, wherein said compound is in the free base form.

6. The methylphenidate compound, according to claim 1, wherein said compound is in the hydrochloride form.

7. A pharmaceutical composition comprising a single isomer methylphenidate compound, selected from the group consisting of the d-threo-enantiomers, and pharmaceutically-acceptable salts thereof, and a pharmaceutically-acceptable diluent or carrier, wherein said compound is in combination with less than about 2% by weight of a contaminant selected from the group consisting of resolving agents and ritalinic acid.

8. The pharmaceutical composition, according to claim 7, wherein said compound is at least about 98% pure.

9. A method for treating a person having a condition susceptible to treatment with methylphenidate comprising administering to the person an effective amount of a single isomer methylphenidate compound selected from the group consisting of d-threo-methylphenidate, and pharmaceutically-acceptable salts thereof, wherein said methylphenidate compound is in combination with less than about 2% by weight of a contaminant selected from the group consisting of resolving agents and ritalinic acid.

10. The method, according to claim 9, wherein said methylphenidate compound is at least about 98% pure.

11. The method, according to claim 9, wherein the condition is selected from the group consisting of attention-deficit hyperactivity disorder and narcolepsy.

* * * * *